United States Patent [19]

Tobkes

[11] 4,038,315
[45] July 26, 1977

[54] ISOLATION AND RECOVERY OF CALCIUM CHLORIDE COMPLEX OF 7-DIMETHYLAMINO-6-DIMETHYL L-6-DEOXYTETRACYCLINE HYDROCHLORIDE

[75] Inventor: Martin Tobkes, Spring Valley, N.Y.

[73] Assignee: American Cyanamid Company, Stamford, Conn.

[21] Appl. No.: 252,175

[22] Filed: May 11, 1972

[51] Int. Cl.$^2$ .................... C07F 3/04; C07C 103/19
[52] U.S. Cl. ............................................ 260/559 AT
[58] Field of Search ................................ 260/559 AT

[56] References Cited

U.S. PATENT DOCUMENTS

| 2,903,395 | 9/1959 | Salivar | 260/559 AT |
| 3,586,483 | 6/1971 | Heider et al. | 260/559 AT |

FOREIGN PATENT DOCUMENTS

| 535,471 | 1/1957 | Canada | |
| 173,888 | 8/1965 | U.S.S.R. | 260/559 AT |

OTHER PUBLICATIONS

Chemical Abstracts, vol. 64, 1966, 1907 a relied on.
Furman et al., "Standard Method of Chemical Analysis", vol. 1, 6th Ed. p. 262.
*Soviet Inventions Illustrated,* Mar. 1966, 173888 relied on.

*Primary Examiner*—Donald G. Daus
*Assistant Examiner*—Mark L. Berch
*Attorney, Agent, or Firm*—Denis A. Polyn

[57] ABSTRACT

This disclosure describes a process for the recovery of 7-dimethylamino-6-demethyl-6-deoxytetracycline from an aqueous solution thereof by means of a calcium chloride complex of 7-dimethylamino-6-demethyl-6-deoxy-tetracycline hydrochloride.

1 Claim, No Drawings

ISOLATION AND RECOVERY OF CALCIUM CHLORIDE COMPLEX OF 7-DIMETHYLAMINO-6-DIMETHYL L-6-DEOXYTETRACYCLINE HYDROCHLORIDE

BRIEF SUMMARY OF THE INVENTION

This invention relates to the recovery of purified 7-dimethylamino-6-deoxytetracycline from aqueous solutions thereof, such as a crystallization mother liquor. More particularly, it concerns the preparation of a calcium chloride complex of 7-dimethylamino-6-demethyl-6-deoxytetracycline hydrochloride and the regeneration therefrom of purified 7-dimethylamino-6-demethyl-6-deoxytetracycline by means of a metathesis reaction.

DETAILED DESCRIPTION OF THE INVENTION

The compound 7-dimethylamino-6-demethyl-6-deoxytetracycline (hereinafter referred to by its generic name "minocycline") is a valuable antibiotic produced by the reductive methylation of 7-(N,N'-dicarbobenzyloxyhydrazino)-6-demethyl-6-deoxytetracycline. This antibiotic and various methods for its preparation and recovery are described in U.S. Pat. No. Re. 26,253, reissued Aug. 15, 1967, to Joseph Petisi and James Howard Boothe.

Conventionally employed methods for the crystallization recovery of minocycline monohydrochloride suffer from a solubility loss in the order of 10 –30 mg./ml., corresponding to yield losses of 6 –18%. The mother liquor in the crystallization of minocycline monohydrochloride contains concentrated impurities, primarily in the form of epi-minocycline. This process is directed to the recovery in good yield of a highly purified form of minocycline monohydrochloride as a calcium chloride complex, from these mother liquors as well as from other aqueous solutions thereof.

It is known that minocycline forms chelates with calcium at pH values above 5.6, containing 1 to 2 moles of calcium per mole of minocycline. These chelates are relatively insoluble in water. Attempts to isolate minocycline calcium chelates from mother liquors in the pH range 7.5 –8.5 resulted in products which were extremely difficult to filter. Furthermore these products contained epi-minocycline in a range of 22–28%.

It has now been discovered that isolation at low pH of about 3.5, in the presence of calcium chloride, results in the recovery of a minocycline hydrochloride-calcium chloride complex having good filtration characteristics and a low epimer content. At a pH of 3.5, material was isolated which filtered well and had an epimer content of only 3.4%. This material exhibited solubility behavior differing from minocycline hydrochloride or its calcium chelates. When isolated from dilute solutions, such as minocycline mother liquors, it begins to crystallize at pH 2.8, redissolves at pH 4.3 –4.4 and reprecipitates at pH 5.8 (presumably as a chelate). In concentrated solution precipitation begins at 1.4. In contrast, minocycline hydrochloride does not begin to precipitate until pH 2.2 and does not begin to redissolve until approximately pH 6.5.

Elemental analysis of the material isolated at pH 3.5 in the presence of calcium chloride agrees with that of a product having the composition (minocycline·HCl)$_4$·CaCl$_2$·$nH_2O$ where $n$ may be an integer from 7 to 13, inclusive, depending upon the degree of drying. The chlorine content of the molecule is too high for a chelate, therefore the compound is a complex of calcium chloride and minocycline hydrochloride. Calcium chelates of tetracyclines are known, as previously mentioned. This product, based upon sprectrophotometric, titrimetric, and elemental analysis is not a chelate but a double salt (or complex) with calcium chloride, possessing $\frac{1}{4}$ mole of calcium chloride per mole of minocycline HCl. Chelates, isolated at higher PH, contain 1 to 2 moles of calcium per mole of minocycline neutral and usually contain no chloride ion.

In practice, the calcium chloride-minocycline hydrochloride complex may be isolated in the pH range 3.1 –4.2, although minimum solubility is obtained in the pH range 3.3 –3.9. The molar ratio of calcium to minocycline may be varied from 0.3 to 1.2, with an optimum range of 0.5 –0.9. The addition of from about 15% to about 20% w./v. of ionizable chloride salts, such as ammonium chloride, sodium chloride, or potassium chloride, depresses the solubility of the complex and appreciably increases the amount of precipitation. The product may be crystallized at temperatures of from about 0° to about 40° C. It will be obvious that similar, but not necessarily optimum, results may be obtained by using other calcium salts such as calcium acetate, calcium nitrate, etc.

Optimum yield and filtration characteristics are obtained by adding the calcium chloride to the minocycline solution at 40° C. and then slowly cooling the solution to 0° C. The suspension is aged a minimum of 2 hours at 0° C. prior to filtration for best results. In this manner, depending upon the percentage of impurities and the potency of the mother liquor, yields of minocycline are obtained ranging from 27 –89% of the spectrophotometric activity in the mother liquor. Typical yields are 60–65%. In all cases the level of impurities in the product is of the order of 3 –4% with epi-minocycline as the major impurity.

The minocycline content of the precipitated complex may be regenerated by a metathesis reaction to break up the complex and to separate the calcium chloride component from the antibiotic component. The separation is achieved by a double decomposition producing a water insoluble calcium salt. For this purpose one may employ hydrofluoric acid, lauric acid, oxalic acid, palmitic acid, or tartaric acid whereby the corresponding water insoluble calcium salts are produced and removed by filtration. The preferred regeneration procedure involves treatment of a dilute hydrochloric acid solution of the complex with oxalic acid, filtering off the resultant calcium oxalate, and adjusting the pH to about 4.0 whereupon minocycline hydrochloride crystallizes from solution.

The invention will be described in greater detail in conjunction with the following specific examples.

EXAMPLE 1

Preparation of Minocycline Monohydrochloride-calcium Chloride Complex

To 250 ml. of mother liquor, derived from recrystallization of minocycline hydrochloride (assaying 32.2 mg./ml. of anhydrous minocycline·HCl), there was added 5.18 gm. of calcium chloride dihydrate. The pH was adjusted to 3.5. The crystals which formed were filtered, washed with 5 ml. of water and dried at 40° C. in vacuo. The yield was 2.66 gm. of material assaying 813 mcg./mg. as anhydrous minocycline hydrochloride (26.9%). The product contained 1.6% calcium and 27.5 mcg./mg epi-minocycline.

EXAMPLE 2:

Preparation of Minocycline Monohydrochloride-calcium Chloride Complex

To a mixture of 18.8 ml. of 0.5 molar calcium chloride and 3.33 ml. of 6N hydrochloric acid there was added 10 gm. of minocycline hydrochloride (assaying 858 mcg./mg. as minocycline neutral). The pH of the mixture was lowered to 1.35 with 6N HCl and to the resultant solution there was added 5N sodium hydroxide in increments. At pH 2.0 the suspension containing precipitate became too thick to stir, requiring the addition of 20 ml. of water. The suspension was then adjusted to pH 3.5, stirred for 1 hour, filtered and the precipitate was dried in vacuo at 35° C. The yield was 9.57 gm. of orange product assaying spectrophotometrically 800 mcg./mg. as minocycline neutral and 864.4 mcg/mg. as anhydrous minocycline hydrochloride (89.3%).

Analysis calculated for $(C_{23}H_{27}N_3O_7 \cdot HCl)_4 \cdot CaCl_2 \cdot 12H_2O$: C, 47.97; H, 5.95; N, 7.30; Cl, 9.24; Ca, 1.74; loss on drying, 9.39; spectrophotometric assay (as anhydrous minocycline hydrochloride), 85.8. Found: C, 48.10; H, 6.15; N, 7.25; Cl, 8.90; Ca, 1.73; loss on drying, 10.25; spectrophotomectric assay, 86.4.

EXAMPLE 3

Preparation of Minocycline Monohydrochloride-calcium Chloride Complex

To 1.5 liters of a minocycline crystallization mother liquor, assaying 10,800 mcg./ml. as minocycline neutral, there was added 225 gm. of sodium chloride and the solution was heated to 40° C. A 31.9 ml. portion of 1 molar calcium chloride solution was added and then the pH was adjusted to 3.5. The mixture was cooled to 5° C. The resultant crystalline suspension was then aged for 6 hours at 5° C. and the product was filtered off. After drying in vacuo at 40° C. there was obtained 15.35 gm. (72.0%) of material assaying 760.2 mcg./mg. as minocycline neutral and containing 1.71% calcium and 17.8 mcg./mg. of epi-minocycline.

EXAMPLE 4

Conversion of Minocycline Hydrochloride Calcium Chloride Complex to Minocycline Hydrochloride In 15.1 ml. of 1N hydrochloric acid there was dissolved 7.56 g. of minocycline hydrochloride calcium chloride complex (assaying 730.4 mcg./mg. as minocycline neutral and containing 1.565% calcium) followed by 484 mg. of oxalic acid dihydrate. The pH of the mixture was adjusted to 1.9 with 5N sodium hydroxide and there was added thereto 80 mg. of Darco G-60. The suspension was stirred 2 hours at 5° C., filtered through Celite and the cake washed with 5.8 ml. of 5% sodium chloride solution. The pH of the combined filterate and wash was adjusted to 4.0 with 5N sodium hydroxide and the resultant suspension of minocycline hydrochloride crystals was aged 1 hour at room temperature and overnight at 5° C. The product was filtered off and washed with 3.8 ml. of 5% sodium chloride solution. The wet crystals were redissolved in 5.12 ml. of a solution prepared by mixing 4.8 ml. of concentrated hydrochloric acid with 29 ml. of water, treated 15 minutes with 90 mg. of Darco G-60 and filtered through Celite . The filter cake was washed with 1.91 ml. of water and the pH of the combined filtrate and wash was adjusted to 4.0 with 5N sodium hydroxide. After aging overnight at 5° C. the product was filtered off, washed with 5.8 ml. of water and dried at 40° C. in vacuo. There was thus obtained 4.28 g. (68.8%) of minocycline hydrochloride assaying 887.1 mcg./mg. as minocycline neutral containing 11.6 mcg./mg. epi minocycline.

I claim:

1. A calcium chloride complex of 7-dimethylamino-6-demethyl-6-deoxytetracycline hydrochloride of the formula:

$(C_{23}H_{27}N_3O_7 \cdot HCl)_4 \cdot CaCl_2 \cdot nH_2O$, wherein $n$ is an integer from 7 to 13, inclusive.

* * * * *